(12) United States Patent
Steffen

(10) Patent No.: US 9,149,251 B2
(45) Date of Patent: Oct. 6, 2015

(54) HINGED REUSABLE ENDOCAVITY NEEDLE GUIDE

(75) Inventor: John Michael Steffen, North Liberty, IA (US)

(73) Assignee: CIVCO MEDICAL INSTRUMENTS CO., INC., Kalona, IA (US)

( * ) Notice: Subject to any disclaimer, the term of this patent is extended or adjusted under 35 U.S.C. 154(b) by 807 days.

(21) Appl. No.: 12/715,732

(22) Filed: Mar. 2, 2010

(65) Prior Publication Data

US 2011/0218444 A1 Sep. 8, 2011

(51) Int. Cl.
*A61B 8/00* (2006.01)
*A61B 8/08* (2006.01)
*A61B 17/34* (2006.01)

(52) U.S. Cl.
CPC ............. *A61B 8/0841* (2013.01); *A61B 8/0833* (2013.01); *A61B 17/3403* (2013.01); *A61B 2017/3405* (2013.01); *A61B 2017/3413* (2013.01)
USPC ........... 600/461; 600/407; 600/437; 600/443; 600/459

(58) Field of Classification Search
CPC ...................... A61B 8/12; A61B 8/445; A61B 2017/00084; A61B 5/0084; A61B 17/3403; A61B 2018/00982; A61B 2018/1425
USPC .................. 600/407, 437, 443–447, 459–472
See application file for complete search history.

(56) References Cited

U.S. PATENT DOCUMENTS

| | | | |
|---|---|---|---|
| 1,222,478 A * | 4/1917 | Sheaff ........................... | 600/220 |
| 4,542,747 A | 9/1985 | Zurinski et al. | |
| 5,052,396 A | 10/1991 | Wedel et al. | |
| 5,623,931 A | 4/1997 | Wung et al. | |
| 6,095,981 A | 8/2000 | McGahan | |
| 6,368,280 B1 | 4/2002 | Cermak et al. | |
| 6,884,219 B1 | 4/2005 | Pruter | |
| 8,073,529 B2 * | 12/2011 | Cermak et al. ................ | 600/424 |
| 2005/0059891 A1 | 3/2005 | Kosaku | |
| 2005/0131301 A1 * | 6/2005 | Peszynski et al. ............ | 600/459 |
| 2010/0041996 A1 * | 2/2010 | Nygaard et al. ............. | 600/459 |

OTHER PUBLICATIONS

International Search Report re Application No. PCT/US2011/026311 dated Apr. 8, 2011.

* cited by examiner

*Primary Examiner* — Mark Remaly
(74) *Attorney, Agent, or Firm* — Caesar Rivise, PC

(57) ABSTRACT

A reusable needle guide suitable for an ultrasonic probe to be use for an endocavity examination of a patient is disclosed. The needle guide basically comprises at least a first and second guide members and a mounting (e.g., clamp) assembly. The clamp assembly serves to releasably mount the needle guide on the probe. The first guide member has a first passageway-forming surface. The second guide member has a second passageway-forming surface. The guide members are connected together to enable them to be pivoted from a closed orientation to an open orientation and vice versa. The first and second passageway-forming surfaces form an elongated passageway to guide a needle therethrough when in the closed orientation. The first and second passageway-forming surfaces are disposed at an angle to each other when they are in the open orientation, whereupon the first and second passageway-forming surfaces can be readily cleaned.

16 Claims, 9 Drawing Sheets

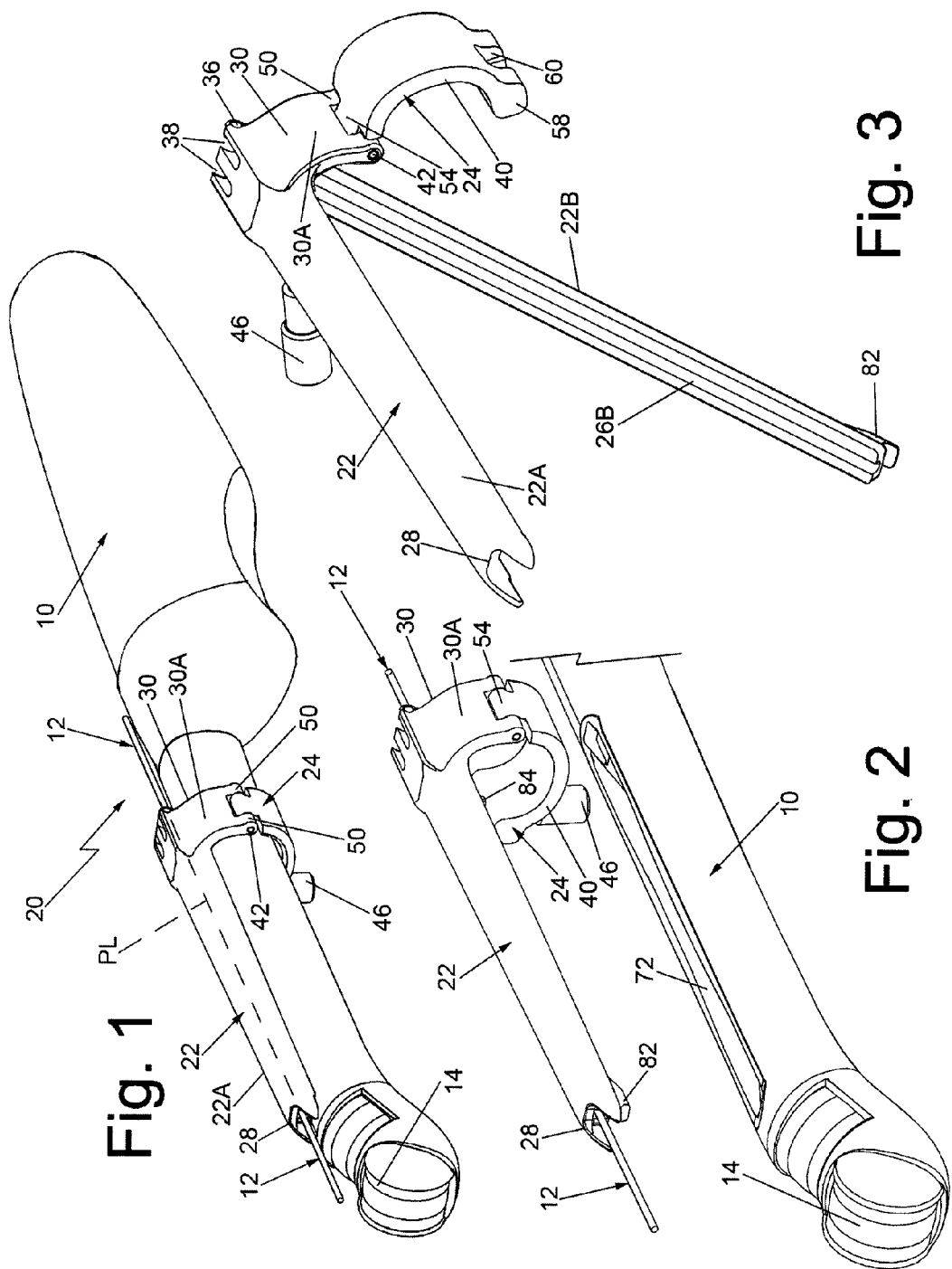

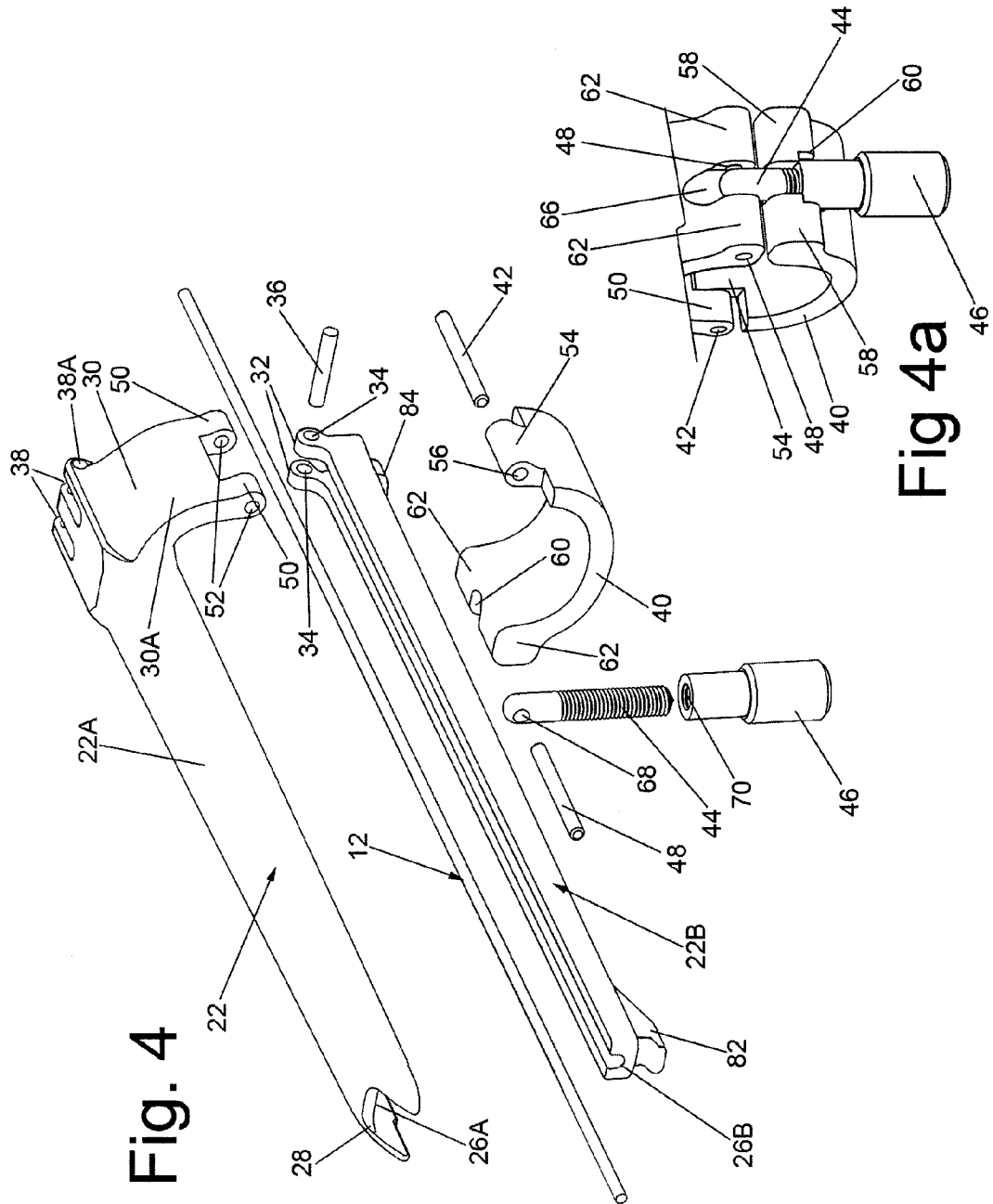

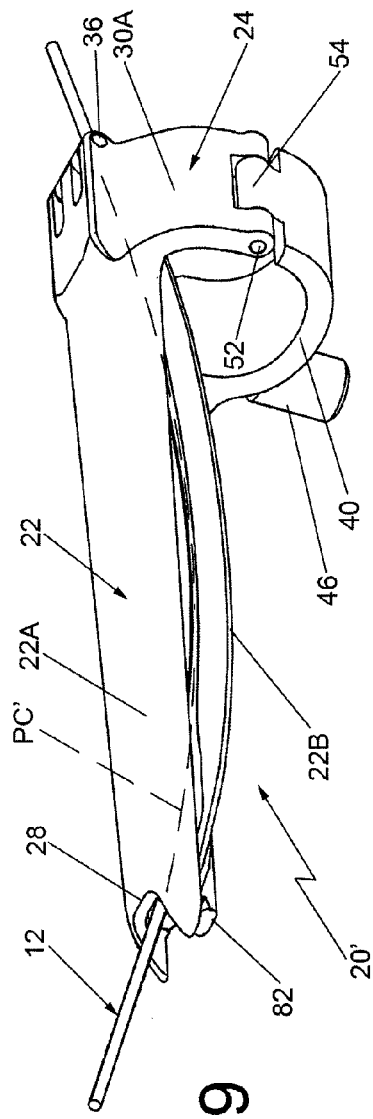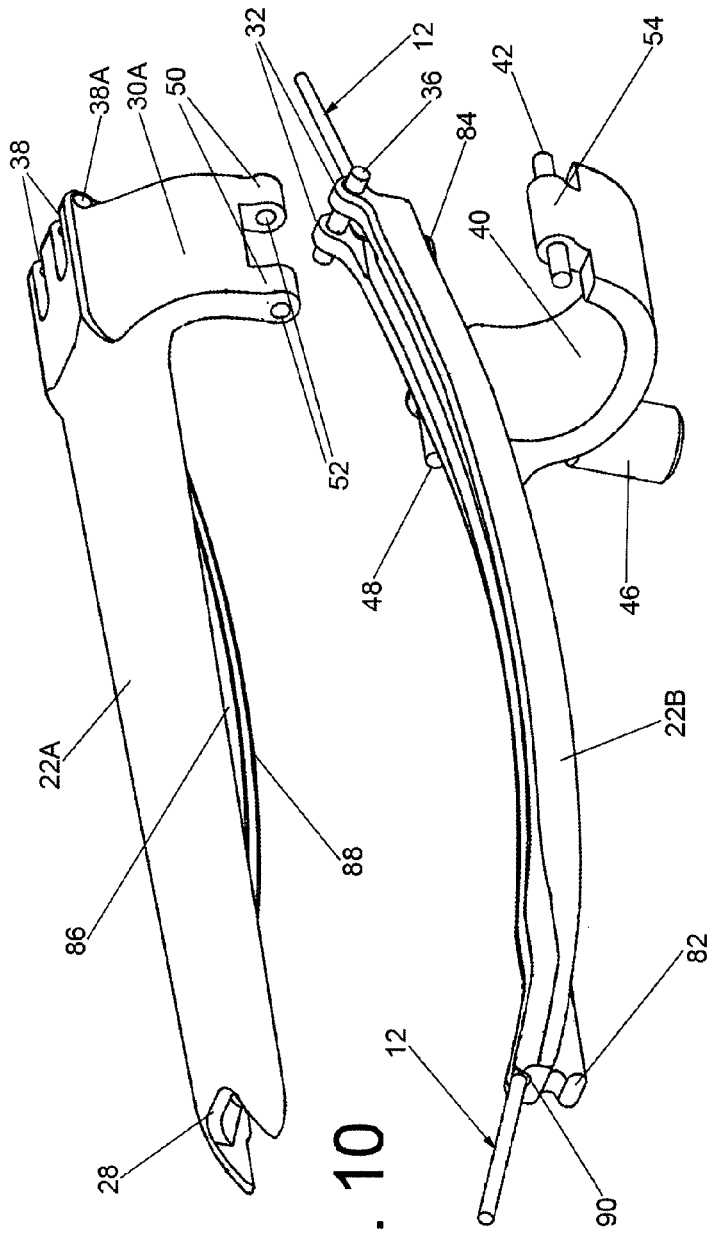

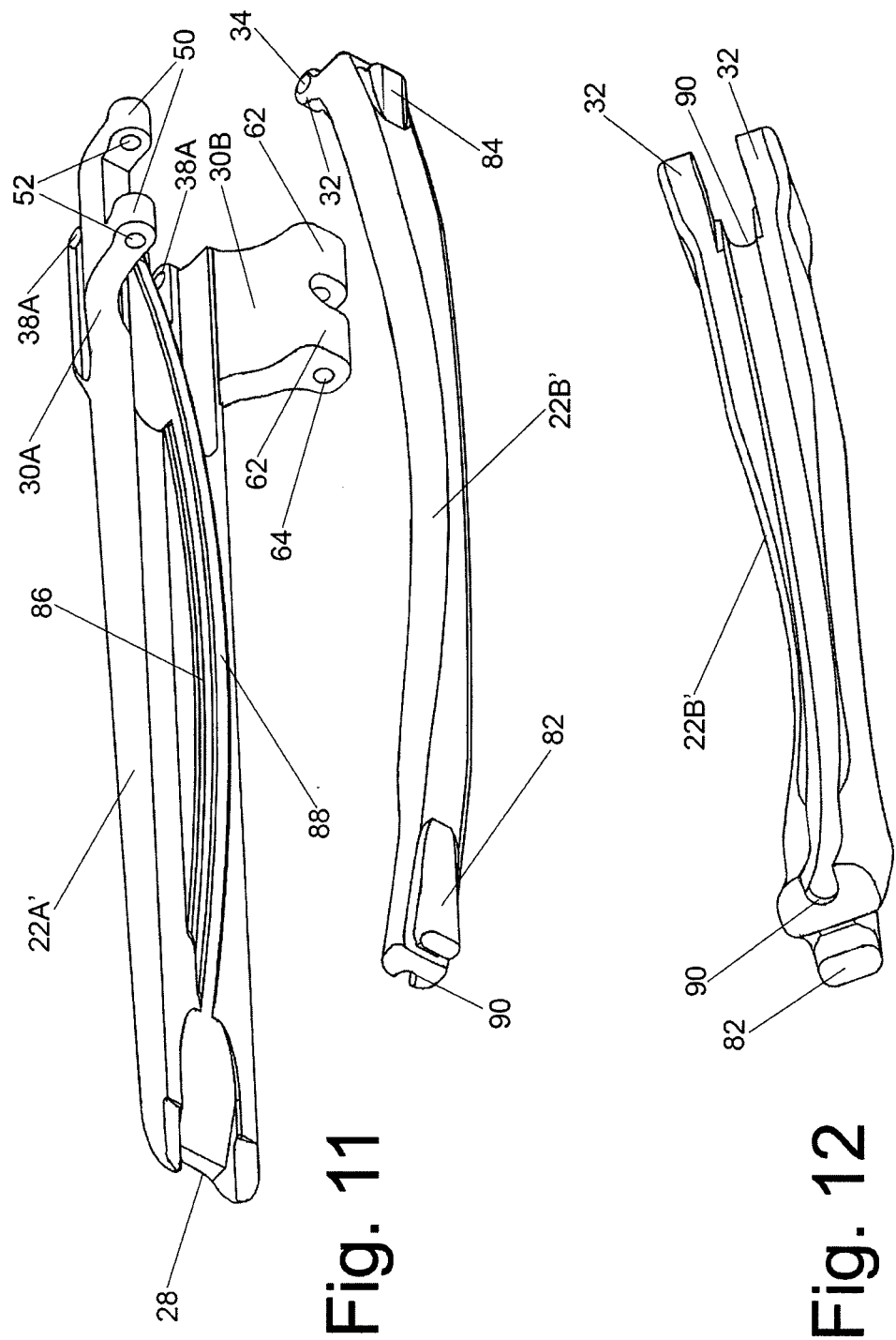

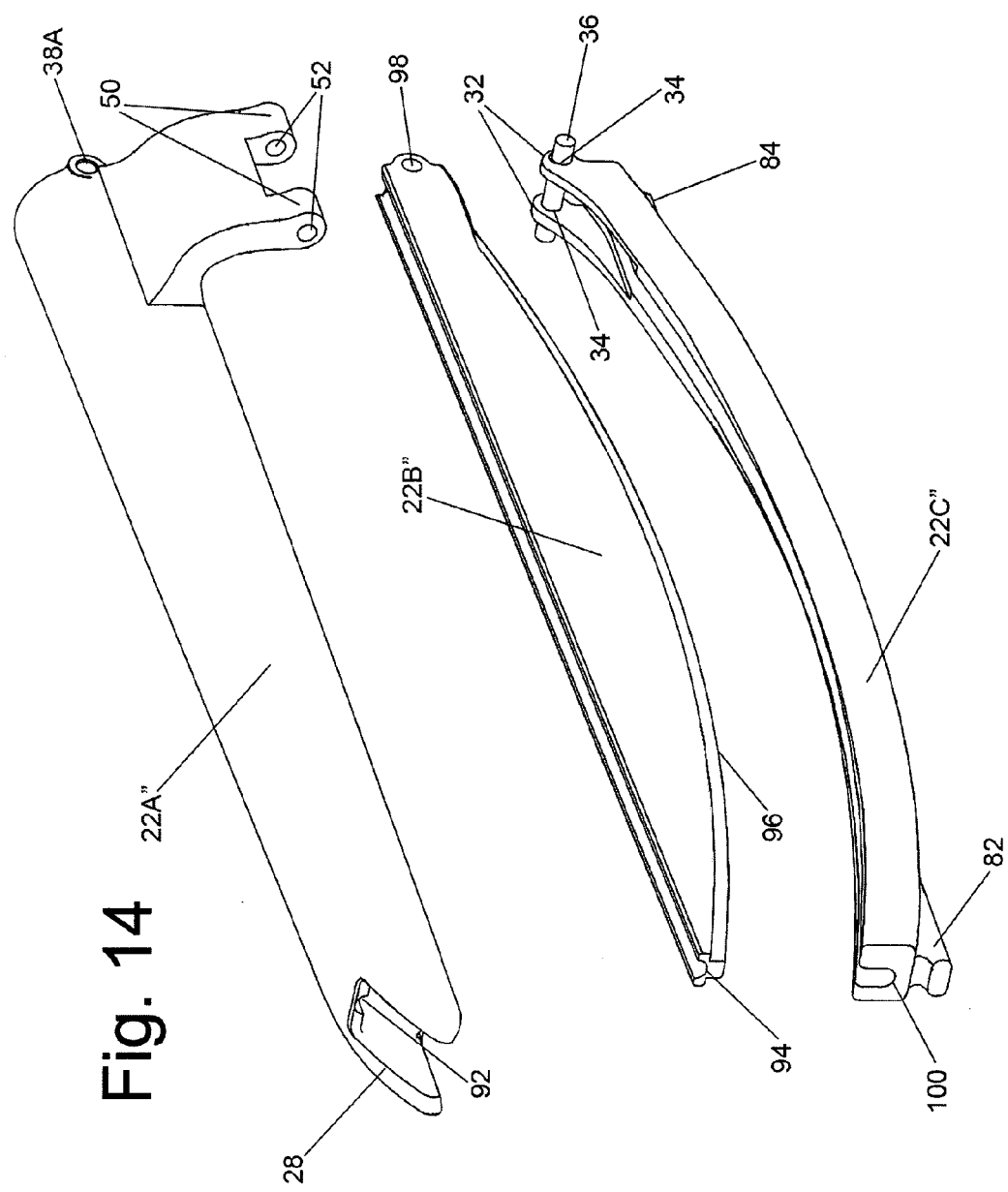

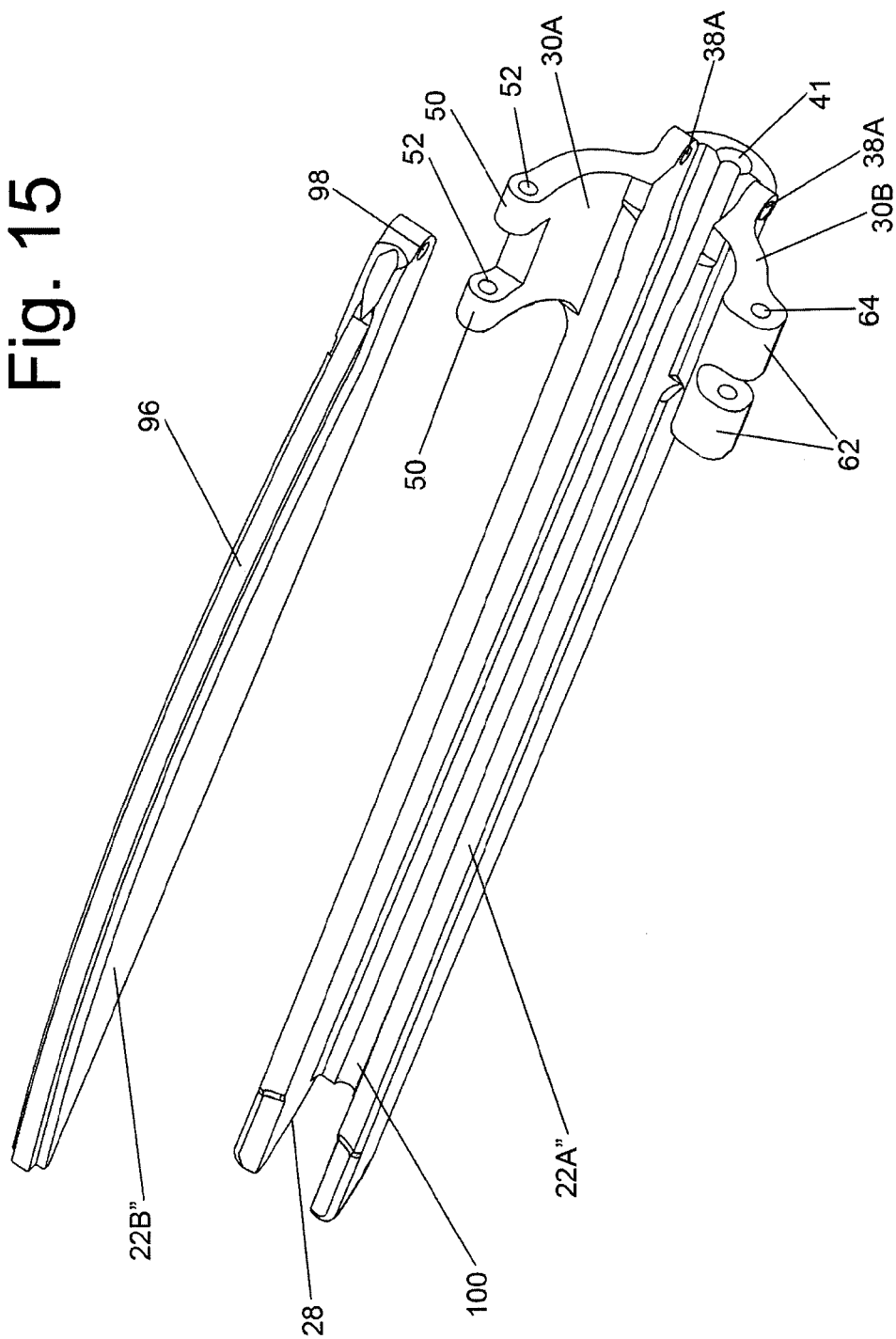

HINGED REUSABLE ENDOCAVITY NEEDLE GUIDE

CROSS-REFERENCE TO RELATED APPLICATIONS n/a

FIELD OF THE INVENTION

This invention relates generally to needle guides for medical imaging instruments and more particularly to devices for guiding needles into selected locations of a patient relative to a medical instrument imaging sensor.

SPECIFICATION

Background of the Invention

Imaging instruments, such as ultrasound probes, have revolutionized the manner in which many important medical procedures are performed. These medical instruments utilize substantially non-invasive imaging techniques to explore and assess the condition of human tissue. As a result of these non-invasive imaging techniques, diagnostic and therapeutic protocols have been developed that allow many highly successful and safe procedures to be performed with a minimum of disturbance to patients. For example, ultrasound probes have become an accepted modality for exploring endocavities, e.g., the human digestive and reproductive tracts, of humans and animals in order to conduct routine examinations, as well as to identify evidence of tumors. In particular, using ultrasound, these tumors can be located and assessed. In conjunction therewith it is frequently desirable and even essential that biopsy samples of the tissue or fluid of a suspected tumor be removed for analysis. To that end, biopsy samples may be taken by carefully directing a hand-held needle, such as a biopsy instrument, catheter, or other thin instrument (hereafter referred to collectively as "needle" or "needles") into the body of a patient in order to remove a tissue sample. It is normally desirable that the needle be guided to a specific position within the body. Unfortunately, hand-held direction of a needle is often inadequate, being both inaccurate and time consuming. Thus, various needle guide devices have been designed for use with ultrasonic probes to assist in directing needles during imaging analysis. Examples of such devices are found in the following U.S. Pat. No. 5,052,396 (Wedel et al.), U.S. Pat. No. 5,623,931 (Wung et al.), U.S. Pat. No. 6,368,280 (Cermak et al.), and U.S. Pat. No. 6,884,219 (Pruter).

Some of the needle guides disclosed in the aforementioned patents and some commercially available needle guides are designed to be mounted on an ultrasonic probe or other imaging instrument that is itself enclosed within a sterile cover, such as a latex film. These covers serve to maintain the ultrasound sensor in a sterile environment, while reducing the likelihood of contamination between patients and also reduce the cost of medical procedures by minimizing sterilization costs.

Some prior art needle guides are designed to be reused. As such they must be suitable for cleaning/sterilization. In particular, the enclosed channel or passageway through which the needle is guided by the guide must have the ability to be cleaned easily and economically. To that end, some available endocavity needle guides are formed of two parts defining the needle-receiving channel or passageway. Such guides commonly make use of two plates or members that slide past each other and lock in the needle channel. The problem with that arrangement is that when they are taken off of the guide and slid apart, they become disassembled in at least two pieces. This presents the potential for loss of a part or damage to a part. In addition, such disassemblable devices require reassembly for reuse, which may constitute a time consuming task.

Consequently, a need exists for an improved needle guide system that will allow a needle to be easily inserted and removed from a patient undergoing imaging (e.g., ultrasound) analysis of a bodily cavity, with a minimum of discomfort to the patient. Such needle guide system should allow the needle to easily and effectively be located at a precise location within a patient to accomplish the desired task, e.g., biopsy tissue. Moreover, the needle guide system should enable the ready mounting and dismounting on the imaging instrument, yet be amenable to be readily cleaned for reuse, without requiring any disassembly and reassembly. Further still it is desirable that the needle guide system permit the use of a sterile cover over the imaging instrument in order to reduce sterilization costs, as well as to improve hygiene.

The subject invention addresses those needs.

BRIEF SUMMARY OF THE INVENTION

In accordance with one aspect of this invention there is provided a reusable needle guide suitable for releasable mounting on an imaging instrument adapted for usage in an endocavity of a patient. The imaging instrument includes a portion adapted for receipt (e.g., mounting) of the needle guide thereon. The needle guide basically comprises a first guide member, a second guide member and a releasable mount for mounting the needle guide on the instrument. The first guide member has a first passageway-forming surface. The second guide member has a second passageway-forming surface. The first and second guide members are pivotably connected together to enable them to be moved from a closed orientation to an open orientation, and vice versa. The first and second passageway-forming surfaces form an elongated passageway therebetween when the first and second guide members are in the closed orientation. The passageway is arranged to enable an elongated needle (or any other elongated device) to be extended through it in a predefined path. The first and second passageway-forming surfaces are disposed at an angle to each other when the first and second guide members are in the open orientation, whereupon the first and second passageway-forming surfaces can be readily cleaned.

In accordance with one aspect of this invention the needle guide is arranged so that the first and second guide members and their respective passageway-forming surfaces to provide a linear path for guiding the needle. In accordance with another aspect of this invention the needle guide is arranged so that the first and second guide members and their respective passageway-forming surfaces to provide a curved path for guiding the needle. In accordance with still another aspect of this invention the needle guide includes three guide members and respective passageway-forming surfaces. That needle guide is arranged so that a first and second of its guide members and their respective passageway-forming surfaces provide a linear path for guiding the needle, while the second and third guide members and their respective passageway-forming surfaces provide a curved path for guiding the needle.

BRIEF DESCRIPTION OF SEVERAL VIEWS OF THE DRAWINGS

FIG. 1 is an isometric view of one exemplary reusable needle guide constructed in accordance with this invention shown in position mounted on a imaging instrument (in this case an ultrasonic transducer or probe) and after having received a conventional needle therein to guide the needle through a linear path to a desired position within the body of a patient;

FIG. 2 is an exploded isometric view of distal end of the imaging instrument and the needle guide of FIG. 1 to show some of the features of the imaging instrument for facilitating the mounting of the needle guide thereon;

FIG. 3 is a somewhat enlarged isometric view of the needle guide of FIG. 1 shown in its open position to facilitate its cleaning/sterilization;

FIG. 4 is an enlarged exploded isometric view, taken obliquely from above, of the needle guide of FIG. 1;

FIG. 4a is an enlarged exploded isometric view showing the clamp assembly of the needle guide of FIG. 1;

FIG. 9 is an isometric view of a second exemplary reusable needle guide, i.e., a curved path needle guide, constructed in accordance with this invention shown after having received a conventional needle therein to guide the needle through a curved path to a desired position within the body of a patient (the imaging instrument on which the needle guide is mounted has not been shown in the interest of drawing simplicity);

FIG. 10 is a slightly enlarged isometric view, taken obliquely from above, of the embodiment of the needle guide of FIG. 9;

FIG. 11 is an isometric view, taken obliquely from below, of the embodiment of the needle guide of FIG. 9;

FIG. 12 is an isometric view, taken obliquely from above, showing the lower guide member of the needle guide of the embodiment of FIG. 9;

FIG. 14 is an isometric view, taken obliquely from above, of the embodiment of the needle guide of FIG. 13 showing its upper guide member, middle guide member and lower guide member, but without showing its clamping assembly for mounting it on the imaging instrument in the interest of drawing simplicity; and FIG. 15 is an isometric view, taken obliquely from below, of the top guide member and middle guide member components of the needle guide of FIG. 13.

DETAILED DESCRIPTION OF THE PREFERRED EMBODIMENTS OF THE INVENTION

Figure 5:
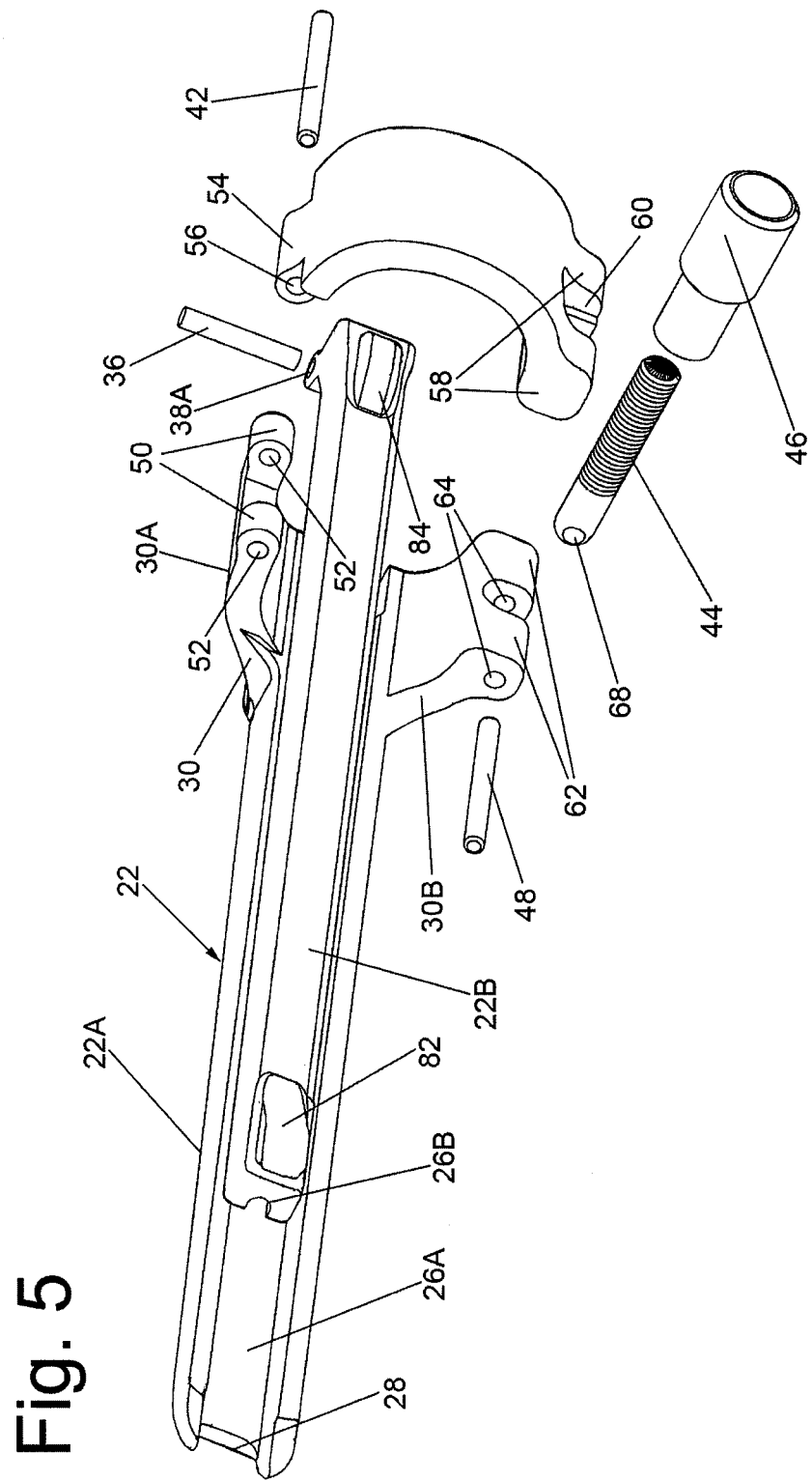
FIG. 5 is an enlarged exploded isometric view, taken obliquely from below, of the needle guide of FIG. 1.
Figure 6:
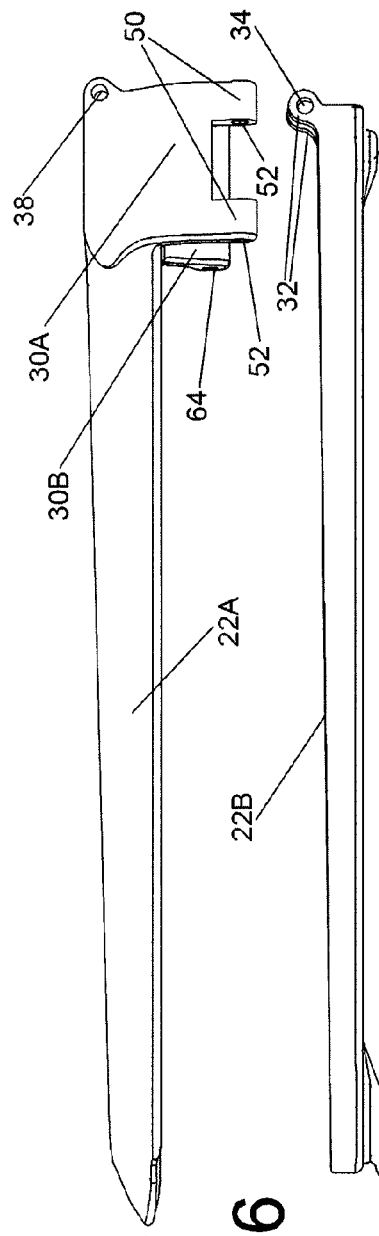
FIG. 6 is an exploded side elevation view of two of the components of the needle guide of FIG. 1, namely its upper guide member and lower guide member.

Referring now to the various figures of the drawing wherein like reference characters refer to like parts, there is shown in FIG. 1 one exemplary reusable needle guide 20 constructed in accordance with this invention. The needle guide 20 is arranged to be releasably mounted on an imaging instrument 10, e.g., an ultrasound transducer or probe, to guide a needle 12 through a desired path for tissue biopsy or any number of medical procedures within an endocavity of a patient (human or animal). To that end, the needle guide 20 basically comprises a guide assembly 22 and a mounting assembly 24. The guide assembly 22 is arranged for receiving the needle and provides a path of a predetermined shape and orientation for guiding that needle to a desired position within the body of the patient so that it can be imaged by the transducer on which the needle guide is mounted. The mounting assembly 24 will be described in detail later. Suffice it for now to state that it is in the form of a clamp for releasably mounting the guide assembly on the imaging transducer.

The term "needle" as used herein means any type of elongated needle, biopsy instrument, catheter, or other thin instrument, that is arranged to be guided to a position inside the body of a patient for performing some type of procedure therein. As will be described in detail later, needle guides constructed in accordance with this invention include portions that are openable to provide ready access for cleaning/sterilization, without requiring disassembly of the device. This feature enables the subject needle guides to be reused economically and thus offers considerable advantages over the prior art.

It should be pointed out at this juncture that the transducer 10 shown in the drawings is a conventional Siemens BP9-4 transducer. That transducer includes a positioning or locating recess (to be described later) for receipt of a correspondingly shaped positioning or locating portion of a needle guide to ensure that the needle guide will be mounted on the transducer at the desired position, e.g., proximally of the transducer's lens 14. To that end, the needle guide 20 is designed specifically for this particular transducer. However, the technology of the needle guides of this invention can be used across other manufacturer's ultrasound transducers (or other imaging instruments), so that the needle guides of this invention can be designed to be transducer-specific, i.e., mate just with one transducer.

Figure 13:
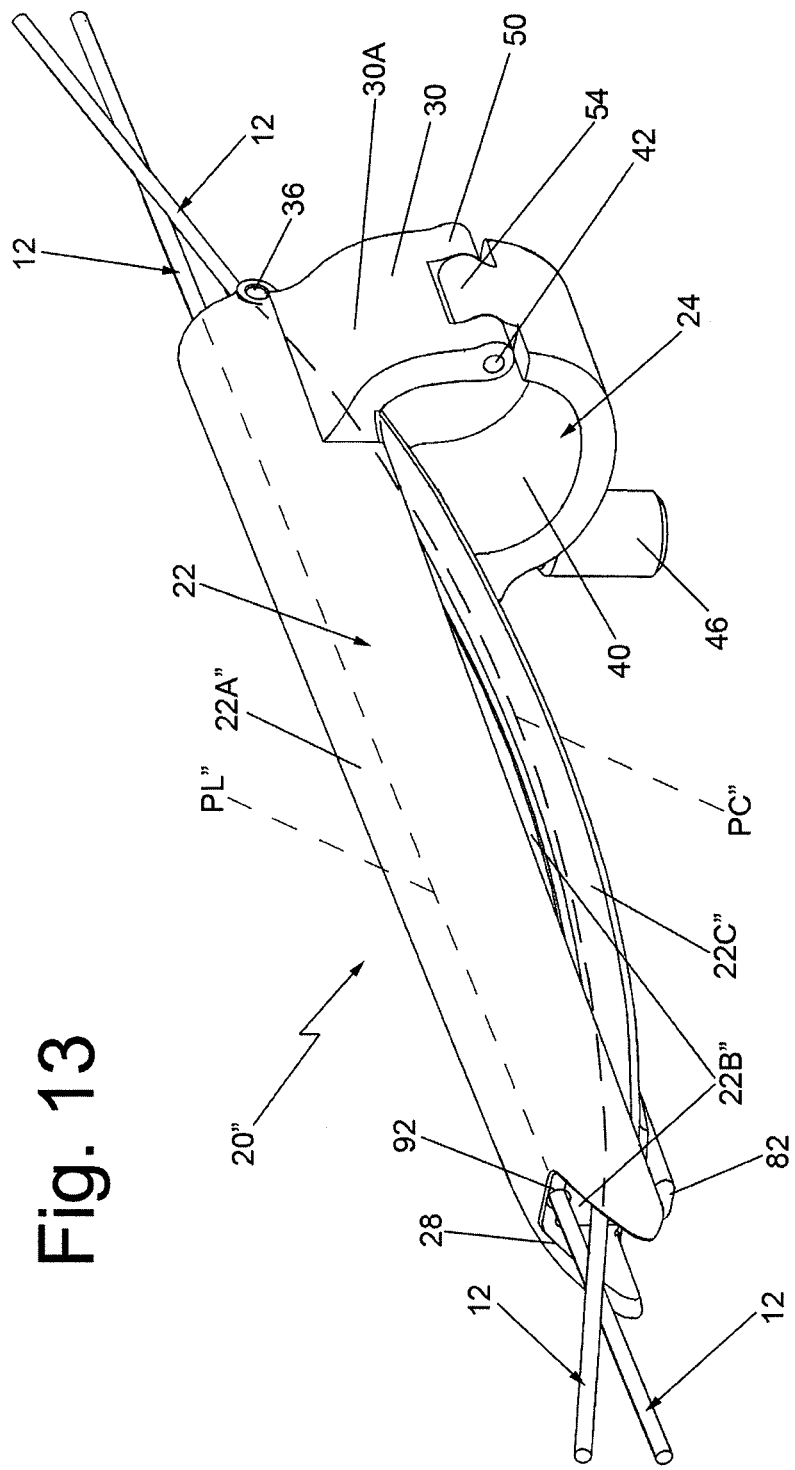
FIG. 13 is an isometric view of a third exemplary reusable needle guide, i.e., a dual path needle guide, constructed in accordance with this invention shown after having received a conventional needle therein to guide the needle through one of two paths, e.g., a linear path or a curved path, to a desired position within the body of a patient (the imaging instrument on which the needle guide is mounted has not been shown in the interest of drawing simplicity)

Moreover, as will be seen and described in detail later, needle guides constructed in accordance with this invention can take various forms/embodiments. For example, the exemplary needle guide embodiment 20 shown in FIGS. 1-8 is arranged to guide a needle in a linear path. In FIG. 9 there is shown a second embodiment 20' wherein the needle guide is arranged to guide the needle through a curved path. In FIG. 13 there is shown still another embodiment 20" wherein the needle guide is arranged to guide a needle through either a linear path or a curved path. In all cases, the needle guide includes a guide assembly made up of plural cooperating guide members that form the path for the needle and which can be moved, e.g., pivoted open, to provide access to the needle guide channel or passageway. In particular, in the embodiment of FIG. 1, the guide assembly includes two cooperating guide members, namely a first guide member 22A and a second guide member 22B. Those guide members are arranged to be moved (pivoted) with respect to each other from and open orientation (shown in FIG. 3) to a closed orientation (shown in FIG. 1), and vice versa. When the guide members 22A and 22B are in the closed orientation, cooperating surfaces (to be described later) of those members conjoin to form a passageway or channel PL (depicted graphically by the broken line in FIG. 1) for receipt and guidance of the needle through it. The passageway or channel defines the needle's linear path with respect to the imaging transducer.

In the embodiment of FIG. 9, the guide assembly of the needle guide 20' includes two cooperating guide members, namely, a first guide member 22A' and a second guide member 22B'. Those guide members are also arranged to be pivoted with respect to each other from an open orientation to a closed orientation, and vice versa. When the guide members 22A' and 22B' are in the closed orientation, cooperating surfaces (to be described later) of those members conjoin to form a curved passageway or channel PC' (depicted by the broken line in that figure) for receipt and guidance of the needle to guide the needle through a curved path with respect to the imaging transducer. In the embodiment of FIG. 13, the guide assembly of the needle guide 20" includes three cooperating guide members, namely, a first guide member 22A", a second guide member 22B" and a third guide member 22C". Those guide members are also arranged to be pivoted with respect to each other from an open orientation to a closed orientation, and vice versa. When the guide members are in the closed orientation, cooperating surfaces (to be described later) of the guide members 22A" and 22B" conjoin to form a linear passageway or channel PL" (depicted by the broken line in that figure) for receipt and guidance of the needle in a linear path, while the guide members 22B" and 22C" conjoin to form a curved passageway or channel PC" (depicted by the broken line in that figure) for receipt and guidance of the needle in a curved path. It should be pointed out at this juncture that the needle guide 20" is arranged to guide only a single needle at a time through either of those paths, e.g., guiding the needle through the linear path PL" or through the curved path PC". Thus, the illustration of FIG. 13, showing two needles being guided at the same time is merely illustrative how a single needle will be guided through either of the respective paths.

Figure 7:
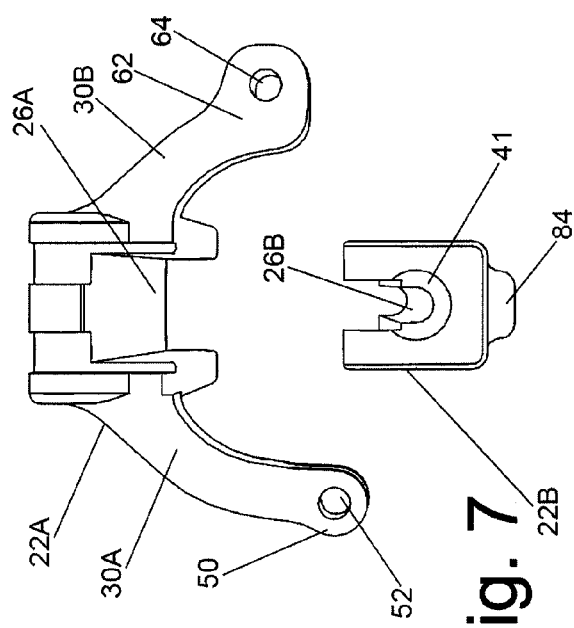
FIG. 7 is an exploded proximal end view of the upper guide member and lower guide member of the needle guide shown in FIG. 6.

Turning now to FIGS. 4-7, the details of the needle guide 20 will now be described. As can be seen the guide member 22A is an elongated member having a linear (in this case planar) undersurface 26A. That surface extends from a notch 28 at the distal end of the member 22A to the proximal end of the member (See FIG. 7). The proximal end of the member 22A is in the form of a yoke 30 having a pair of extending arcuate legs 30A and 30B. The legs 30A and 30B also form a portion of the clamp assembly 24. The guide member 22B is an elongated member having an upper surface in the form of a linear groove 26B extending from the distal end of the member 22B to its proximal end. As best seen in FIGS. 4 and 7 the cross section of the groove 26B is semicircular terminating in an opposed pair of upstanding tangential walls. The proximal end of the guide member 22B includes a spaced apart pair of projections or ears 32. Each of the ears includes an opening 34. The openings are aligned with each other and extend perpendicularly to the longitudinal axis of the member 22B for receipt of a hinge pin 36 to pivotally connect the guide member 22B to the guide member 22A. The guide member 22A includes a pair of notches 38 at its proximal end for receipt of respective ones of the ears 34. The portions of the guide member 22A contiguous with the notches include aligned openings 38A for receipt of the hinge pin 36. Accordingly when the openings 34 in the ears of the guide member 22B are aligned with the openings 38A in the proximal end of the guide member 22A and the hinge pin 36 is extended through those aligned openings, the guide members 22A and 22B will be pivotably connected to each other. This enables one to readily pivot the guide member 22B with respect to the guide member 22A from the closed position shown in FIG. 1 to an open position shown in FIG. 3, and vice versa. It should be noted that the open position as shown in FIG. 3 constitutes an angle of approximately 45 degrees between the two guide members 22A and 22B. That is merely exemplary of various open positions that the guide members may take with respect to each other since the amount that they can pivot about the hinge pin 36 is well over 180 degrees. Thus, ready access to all of the interior and exterior surfaces of the guide members can be achieved without any disassembly of the needle guide, by merely pivoting its two guide members with respect to each other to any desired angular orientation.

Figure 8:
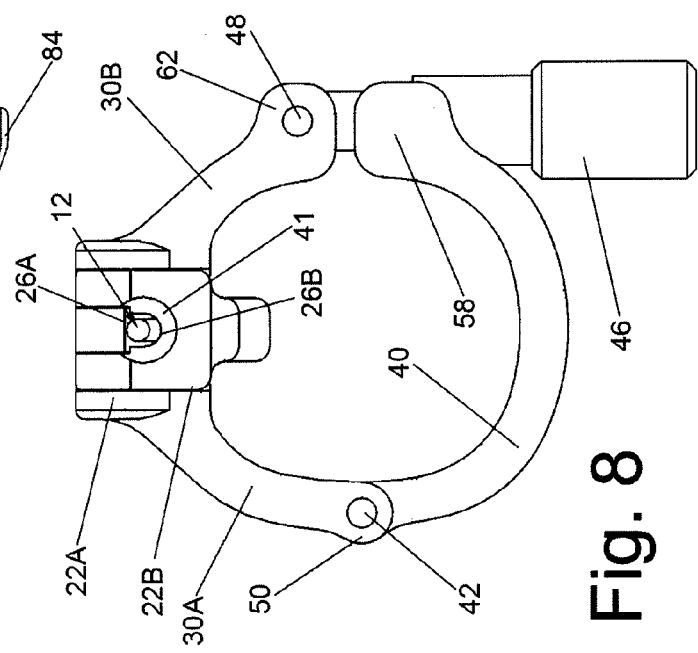
FIG. 8 is a proximal end view of the upper guide member and lower guide member of the needle guide and the mount, e.g., clamp assembly, of the needle guide for releasably mounting it on the imaging instrument.

When the guide members 22A and 22B are in the closed position, the elongated planar surface 26A of the guide member 22A and the elongated surface of the groove 26B conjoin as best seen in FIG. 8 to form an enclosed passageway or channel through which the needle can be extended to guide it in a linear path PL with respect to the transducer 10. The entry to the channel is at the proximal end of the guide 20 and includes a funnel shaped mouth or entryway 41 (See FIG. 8) to facilitate insertion of the distal end of a needle therein.

As mentioned above, the guide member 20 is arranged to be releasably mounted on the probe 10 by the mounting assembly 24. That assembly is best seen in FIGS. 4 and 4a and basically comprises a clamp member 40, a hinge pin 42, a screw 44, a thumb knob 46, a locking pin 48 and the heretofore identified legs 30A and 30B of the guide member 22A. The clamp member 40 is a semi-circular shaped member arranged to be pivotably connected to the leg 30A of the guide member 22A. The leg 30A of the guide member 22A includes a spaced pair of projections or ears 50. Each of the ears includes an opening 52. The openings are aligned with each other and extend parallel to the longitudinal axis of the guide member 22A. The clamp member 40 includes a projection 54 extending from one end. The projection includes an opening 56 extending therethrough. The projection 54 is arranged to be located between the ears 50 of the guide member 22A so that the opening 56 is aligned with the openings 52. The hinge pin 42 is inserted in the aligned openings to pivotably connect the clamp member 40 to the guide member 22A. The free end of the clamp member 40 is in the form of a thickened flange 58 including an undercut notch 60 (FIG. 4a) in its center.

The free end of the clamp member 40 is arranged to be releasably secured to the leg 30B of the guide member 22A to form a ring encircling a portion of the ultrasonic probe therein. The ring is arranged to be tightened (as will be explained hereinafter) to clamp the needle guide in place on the instrument. To that end the leg 30B of the guide member 22A includes a spaced pair of projections or ears 62. Each of the ears includes an opening 64 (FIG. 7). The openings 64 are aligned with each other and extend parallel to the longitudinal axis of the guide member 22A. The space or gap 66 between the ears 62 is arranged to receive the top portion of the screw 44. The screw 44 includes an opening 68 at its upper end through which the locking pin 48 extends. The locking pin also extends through the aligned openings 64 in the guide member 22A, thereby pivotably connecting the screw 44 to the guide member 22A. The bottom end of the screw includes an external thread arranged to be received within an internally threaded bore 70 (FIG. 4) in the thumb knob 46. With the screw threadedly engaged in the bore 70 the screw and knob together form what can be called a thumb-screw. As best seen in FIG. 7, the thumb-screw is arranged to be located within the undercut recess 60 and tightened to bring the clamp member 40 closer to the guide member and thereby tightly clamp the needle guide 20 onto the ultrasonic probe 10.

In order to ensure that the needle guide is at the desired position and orientation on the probe, the probe includes the heretofore mentioned positioning recess. That recess is designated by the reference number 72 and basically comprises an elongated longitudinally extending recess whose depth increases from each end to the center (i.e., the bottom surface of the recess is in the form of a curve. The shape of that curve is chosen to mate with the guide member 22B' of the needle guide 20' and to mate with the guide member 22C" of the needle guide 20" in addition to accommodating a portion of the guide member 22B of the needle guide 20. Thus, the probe 10 can accommodate (mount) any of the needle guides shown herein.

At the front or distal end of the locating recess 72 is a cavity (not shown) whose profile is configured to mate with a projection 82 (FIGS. 4 and 6) located on the distal end of the guide member 22B. The proximal end of the guide member 22B includes another projection 84, which is arranged to be disposed within a correspondingly shaped cavity at the proximal end of the recess 72 in the probe. Accordingly, the mounting of the needle guide 20 on the probe 10 is as follows. The clamp assembly is opened by unscrewing the thumb-screw so that it is not within the undercut recess 60 in the clamp member 40. This frees the free end of the clamp member 40, enabling it to swing freely. The guide member 22B is seated within the locating recess 72 of the ultrasonic probe by inserting its projection 82 within the cavity of the probe's locating recess at the distal end of that recess and then orienting the guide member 22 so that the projection 84 at the proximal end of the guide member is received within the correspondingly shaped cavity at the proximal end of the locating recess 72. The guide member 22A can then be pivoted downward so that its passageway-forming surface 26A conjoins with the passageway forming surface of the recess 26B in the guide member 22B to form the passageway or channel to guide the needle 12. The clamp member 20 can then be swung upward so that its free end flange 58 is located immediately adjacent the ears 62 of the guide member 22A. The thumb-screw can then be swung downward so that it is located within the undercut recess 60 and then tightened as shown in FIG. 4a, thereby releasably securing the needle guide onto the ultrasonic probe.

As will be appreciated by those skilled in the art, if desired a thin, flexible sheath or other cover (e.g., a latex condom shaped sheath) can be placed over the ultrasonic probe before the needle guide is mounted thereon to keep the instrument sanitary.

In any case, the probe with the needle guide thereon is now ready for use. To that end, the ultrasound probe with the needle guide thereon is inserted as a unit through a natural orifice, e.g., into the rectum, so that the proximal portion of the needle guide is located just outside of the patient. The ultrasound probe provides an image of the anatomy of interest. When the probe has imaged an area of interest, e.g., an area of the prostate to be biopsied, the needle 12 is inserted into and through the guide. In particular, the distal end of the needle 12 is inserted into the flared mouth 41 of the guide passageway and down the passageway until the distal end of the needle is at the desired position to take the biopsy sample. The probe 10 provides images of the movement of the needle to and into that tissue.

Once the biopsy procedure has been completed the needle 12 is removed by withdrawing it from the needle guide 20. The probe 10 and needle guide 20 are then removed as a unit from the patient. The needle guide 20 can then be disconnected (dismounted) from the probe for cleaning/sterilization or any other desired processing. To that end, the thumb-screw is loosened, thereby enabling it to be removed from the undercut recess 60 in the guide member 22A. This frees the clamp member so that it can be swung downward, thereby opening the clamp and enabling the needle guide to be taken off of the probe. When the needle guide is free of the probe, its two guide members 22A and 22B can be pivoted apart, i.e., moved to an open position shown in FIG. 3, since both are freely mounted on the hinge pin 36. With the needle guide in the open state all of its internal surface are readily accessible for cleaning or other processing. After such cleaning or processing, the needle guide can be remounted on the probe for another procedure.

Referring to FIG. 9, the embodiment of the needle guide 20' will now be discussed. It should be pointed out at this juncture that the needle guide 20' is in many respects similar to the needle guide 20, except for the features forming its curved path. Thus, for example, the needle guide 20' includes the same structure for releasably mounting (clamping) it to the ultrasonic probe 10. In the interest of brevity those components which are common to the needle guides 20 and 20' will be given the same reference numbers and the features of their construction and operation will not be reiterated.

The guide member 22A' is an elongated member similar in shape to guide member 22A, except that it includes a downwardly projecting, longitudinally extending wall 86, whose bottom edge is in the form of a curved surface 88. That surface is its passageway-forming surface and arranged to conjoin with a surface of the guide member 22B' to form the curved passageway PC'. To that end, the guide member 22B' is an elongated member of curved shape corresponding to the curve of the surface 88 of the guide member 22A'. The guide member 22B' includes an elongated, longitudinally extending groove 90 which is similar in cross section to the groove 26B of the guide member 22B. The inner surface of the groove forms the passageway-forming surface which conjoins with the surface 88 of the guide member 22A' to form the curved passageway PC' when the guide members 22A' and 22B' are in their closed position.

As will be appreciated by those skilled in the art, the curved path created by the passageway PC' requires the needle to curve, but the needle is sufficiently flexible, e.g., is of 16 to 18 gauge stainless steel, to negotiate the curve, so that it exits the needle guide with an upward sweep. This arrangement is of particular utility for conducting a biopsy of the prostate, since it enables the taking of the sample above the ultrasound lens 14. Taking such a sample with a straight needle is a bit more difficult to accomplish, e.g., the physician may have to "crank down" on the ultrasound transducer to position the straight needle path in an upward angle, which action may result in some discomfort for the patient.

Referring to FIG. 13, the embodiment of the dual-path needle guide 20" will now be discussed. It should be pointed out at this juncture that the needle guide 20" is in many respects similar to the needle guides 20 and 20', except for the features forming its linear path and its curved path. Thus, for example, the needle guide 20" includes the same structure for releasably mounting (clamping) it to the ultrasonic probe 10. In the interest of brevity those components which are common to the needle guides 20, 20' and 20" will be given the same reference numbers and the features of their construction and operation will not be reiterated.

The guide member 22A" is an elongated member similar in shape to guide member 22A, except that it does not include the planar undersurface 26A. Instead the guide member 22A" includes a linear groove 92 extending the length of the guide member from the notch 28 to the proximal end of the guide member. The groove 92 is of semicircular cross section as best seen in FIG. 15 and its inner surface forms its passageway-forming surface, i.e., one portion of the passageway PL" created when the guide members 22A" and 22B" are in their closed position. The guide member 22B" is an elongated member that is shaped similar to the projecting wall of the guide member 22A'. In particular, the guide member 22B" includes a top edge bearing a linear groove 94 extending the length of the guide member 22B". As best seen in FIG. 14 the groove 94 is of semicircular cross section and of the same radius as groove 92 of the guide member 22A". The inner surface of the groove 94 forms its passageway-forming surface which conjoins with the passageway-forming surface groove 92 of the guide member 22A' to form the passageway PL" when the guide members 22A' and 22B' are in their closed position. The proximal end of the guide member 22B" includes an opening 98 which is arranged to receive the pivot pin 36 to enable the guide member 22B" to be pivoted with respect to the guide members 22A" and 22C". The guide member 22B" also includes a bottom edge in the form of a curved surface 96. That surface is similar to the surface 88 of member 22B' and forms that member's passageway-forming surface which is arranged to conjoin with a surface of the guide member 22C" to form the curved passageway PC".

The guide member 22C" is an elongated member similar to the guide member 22B'. In particular, the guide member 22C" includes an elongated, longitudinally extending groove 100 that is similar in cross section to the groove 90 of the guide member 22B'. The inner surface of the groove 100 forms that member's passageway-forming surface which conjoins with the surface 96 of the guide member 22B" to form the passageway PC" when the guide members 22B" and 22C" are in their closed position. The pivot pin 36 extends through the openings 34 in the ears 32 of the guide member 22C", through the aligned opening 98 in the guide member 22B" and through the aligned openings 38A in the guide member 22A" to enable those guide members to be pivoted with respect to each other from an open position to a closed position, and vice versa.

It should be pointed out at this juncture that the three needle guides 20. 20' and 20" are merely exemplary of a myriad of needle guides that can be constructed in accordance with this invention to form one or plural paths (whether linear or curved) dependent on the specific transducer requirement. In this regard the needle guide components have channel specific geometry to provide a path for needle guidance, with the number and geometry being dependent upon transducer geometry and needle path requirements. In fact, the needle guides can be constructed to establish more than two paths, if desired, providing that the guide members forming the guide assembly can be pivoted with respect to one another to enable them to be opened to provide ready access to their interior portions forming the needle guide channel.

Thus, with the subject invention a user is able to readily collapse the guide assembly and attach the needle guide to the transducer for use, or fan the guide assembly components open around the hinge for cleaning them. When the guide assembly is open, the user can readily access the needle path channels for easy cleaning, without concern that any components will become misplaced, since all are always connected to one another.

It should also be pointed out that while the means for releasably mounting the needle guide on the imaging instrument is shown and has been described as constituting a clamping assembly, that is merely exemplary of various mechanisms that can be used to achieve that end.

Without further elaboration the foregoing will so fully illustrate my invention that others may, by applying current or future knowledge, adopt the same for use under various conditions of service.

What is claimed is:

1. A reusable endocavity needle guide arranged for releasable mounting on an imaging instrument, comprising: a first guide member, a second guide member and a releasable mounting assembly for mounting on an imaging instrument, said first guide member having a first elongated passageway-forming surface having a first longitudinal axis, said second elongated guide member having a second passageway-forming surface having a second longitudinal axis, said first and second guide members being pivotably connected together to pivot about a transverse axis extending generally perpendicularly to said first and second longitudinal axes to enable said first and second guide members to be pivoted with respect to each other about said transverse axis from a closed orientation to an open orientation, and vice versa, said first and second passageway-forming surfaces forming an elongated passageway therebetween when said first and second guide members are in said closed orientation, said releasable mounting assembly maintaining said first and second guide members in said closed orientation when said releasable mounting assembly is mounted to the imaging instrument, said passageway being arranged to enable an elongated needle or other elongated device to be extended therethrough in a predefined path, said first and second passageway-forming surfaces being disposed at an angle to each other when said first and second guide members are in said open orientation when said releasable mounting assembly is disconnected from the imaging instrument, whereupon said first and second passageway-forming surfaces can be readily cleaned.

2. The needle guide of claim 1 wherein said first and second guide members are connected together at a hinge joint.

3. The needle guide of claim 1 wherein said mounting assembly is arranged to clamp said needle guide onto the portion of the imaging instrument.

4. The needle guide of claim 3 wherein said mounting assembly comprises a pair of curved shaped members arranged to encircle the portion of the imaging instrument.

5. The needle guide of claim 4 wherein said releasable mount additionally comprises a thumb-screw to tighten said pair of curved shaped members about the portion of the imaging instrument.

6. The needle guide of claim 1 wherein said elongated passageway is linear.

7. The needle guide of claim 1 wherein said elongated passageway is curved.

8. The needle guide of claim 1 wherein said needle guide includes a locating member arranged to mate with a portion of the imaging instrument to precisely position said needle guide on the instrument.

9. The needle guide of claim 8 wherein said locating member comprises a projection.

10. A reusable endocavity needle guide arranged for releasable mounting on an imaging instrument, said needle guide being adapted for mounting on the instrument and comprising a first guide member, a second guide member, a third guide member and a releasable mounting assembly for mounting on an imaging instrument, said first guide member having a first elongated passageway-forming surface having a first longitudinal axis, said second elongated guide member having a second passageway-forming surface having a second longitudinal axis and a third passageway-forming surface having a third longitudinal axis, said third guide member having a fourth passageway-forming surface having a fourth longitudinal axis, said first and second guide members being pivotably connected together to pivot about a transverse axis extending generally perpendicularly to said first, second, third and fourth axes to enable said first and second guide members to be pivoted with respect to each other about said transverse axis from a closed orientation to an open orientation, and vice versa, said second and third guide members being pivotably connected together to pivot about said transverse axis to enable said second and third guide members to be pivoted with respect to each other about said transverse axis from a closed orientation to an open orientation, and vice versa, said first and second passageway-forming surfaces forming a first elongated passageway therebetween when said first and second guide members are in said closed orientation, said releasable mounting assembly maintaining said first and second guide members in said closed orientation when said releasable mounting assembly is mounted to the imaging instrument, said first passageway being arranged to enable an elongated needle or other elongated device to be extended therethrough, said third and fourth passageway-forming surfaces forming a second elongated passageway therebetween when said second and third guide members are in said closed orientation, said releasable mounting assembly also maintaining said second and third guide members in said closed orientation when said releasable mounting assembly is mounted to the imaging instrument, said second elongated passageway being arranged to enable an elongated needle or other elongated device to be extended therethrough, said first and second passageway-forming surfaces being disposed at an angle to each other when said first and second guide members are in said open orientation when said releasable mounting assembly is disconnected from the imaging instrument, whereupon said first and second passageway-forming surfaces can be readily cleaned, said third and fourth passageway-forming surfaces being disposed at an angle to each other when said second and third guide members are in said open orientation when said releasable mounting assembly is disconnected from the imaging instrument, whereupon said third and fourth passageway-forming surfaces can be readily cleaned.

11. The needle guide of claim 10 wherein one of said first and second passageways is linear and the other of said first and second passageways is curved.

12. The needle guide of claim 11 wherein said first, second and third guide members are connected together at a hinge joint.

13. The needle guide of claim 10 wherein said mounting assembly is arranged to clamp said needle guide onto the portion of the imaging instrument.

14. The needle guide of claim 13 wherein said mounting assembly comprises a pair of curved shaped members arranged to encircle the portion of the imaging instrument.

15. The needle guide of claim 14 wherein said releasable mount additionally comprises a thumb-screw to tighten said pair of curved shaped members about the portion of the imaging instrument.

16. The needle guide of claim 10 wherein said needle guide includes a locating member arranged to mate with a portion of the imaging instrument to precisely position said needle guide on the instrument.

* * * * *